United States Patent [19]

Bugaut et al.

[11] 4,084,052
[45] Apr. 11, 1978

[54] DIAMINOBENZOQUINONES

[75] Inventors: Andreè Bugaut, Boulogne-sur-Seine; Monique Laudon, Gagny, both of France

[73] Assignee: L'Oreal, Paris, France

[21] Appl. No.: 762,272

[22] Filed: Jan. 25, 1977

Related U.S. Application Data

[62] Division of Ser. No. 600,786, Jul. 31, 1975, Pat. No. 4,023,926, which is a division of Ser. No. 370,737, Jun. 18, 1973, Pat. No. 3,919,265.

[30] Foreign Application Priority Data

Jun. 21, 1972 Luxembourg .......................... 65555
Jan. 23, 1973 Luxembourg .......................... 66883

[51] Int. Cl.$^2$ .................. C07D 211/14; C07D 295/12
[52] U.S. Cl. ..................................... 544/165; 544/166; 260/293.76; 260/293.79
[58] Field of Search ............................... 544/165, 166; 260/293.76, 293.79

[56] References Cited

U.S. PATENT DOCUMENTS 3,919,265  11/1975  Bugaut et al. ................... 260/293.79
4,023,926  5/1977   Bugaut et al. ................... 260/293.79

OTHER PUBLICATIONS

Bugaut et al., "Chem Abstracts" vol. 80 (1974), No. 134937w.
Ghilardi et al., "Chem Abstracts" vol. 81 (1974) No. 29470m.

Primary Examiner—Henry R. Jiles
Assistant Examiner—R. W. Ramsuer
Attorney, Agent, or Firm—Cushman, Darby & Cushman

[57] ABSTRACT 2,5-diamino-1,4-benzoquinones are used in the production of hair dye compositions and can be prepared by condensing a corresponding 3-amino-4-methoxy phenol derivative on one of a corresponding hydroxy aniline or phenylenediamine derivative, a corresponding benzoquinone imine derivative or a corresponding nitroso derivative.

2 Claims, No Drawings

DIAMINOBENZOQUINONES

This is a division, of application Ser. No. 600,786 now U.S. Pat. No. 4,023,926 filed July 31, 1975 which is a division of Ser. No. 370,737 filed June 18, 1973, now U.S. Pat. No. 3,919,265.

The present invention relates to new 2,5-diamino-1,4-benzoquinones of the formula:

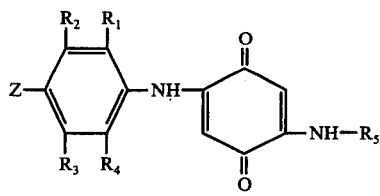

wherein $R_1$, $R_2$, $R_3$ and $R_4$, each independently represent a member selected from the group consisting of hydrogen, halogen, lower alkyl having 1–4 carbon atoms and lower alkoxy having 1–4 carbon atoms; $R_5$ represents a member selected from the group consisting of hydrogen, lower alkyl containing 1–4 carbon atoms and lower alkyl having 1–4 carbon atoms and substituted with a member selected from the group consisting of hydroxyl and

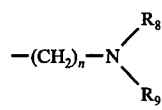

wherein $n$ is 2–6 and preferably 2, and $R_8$ and $R_9$ each independently are selected from the group consisting of hydrogen, alkyl having 1–4 carbon atoms and alkyl having 1–4 carbon atoms and substituted by a member selected from the group consisting of hydroxy and acylamino wherein the acyl is aliphatic having 2–5 carbon atoms or $R_8$ and $R_9$ together with the nitrogen atom to which they are attached form a six-membered heterocycle capable of including an oxygen heteroatom such as piperidinyl or morpholinyl; and Z represents a member selected from the group consisting of hydroxyl,

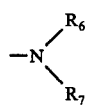

wherein $R_6$ and $R_7$ each independently represent a member selected from the group consisting of hydrogen, lower alkyl having 1–4 carbon atoms and lower alkyl having 1–4 carbon atoms and substituted by a member selected from the group consisting of hydroxyl, carbamyl, acylamino wherein acyl has the meaning given above, mesylamino and benzoylamino, and

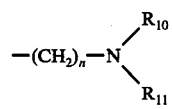

wherein $n$ represents 2–6, preferably 2, and $R_{10}$ and $R_{11}$ each independently represent a member selected from the group consisting of lower alkyl having 1–4 carbon atoms, lower alkyl having 1–4 carbon atoms and substituted by a member selected from the group consisting of hydroxyl and acylamino wherein acyl has the meaning given above, and $R_{10}$ and $R_{11}$ together with the nitrogen atom to which they are attached form a six-membered heterocycle capable of including an oxygen heteroatom, such as piperidinyl or morpholinyl.

The present invention also relates to the salts of the compounds of formula I with mineral or organic acids such as the hydrochloride, hydrobromide, and sulfate thereof and to the quaternary ammonium salts of those compounds which have a tertiary amino group.

The compounds of the present invention can be prepared by condensing a 3-amino-4-methoxy phenol of the formula

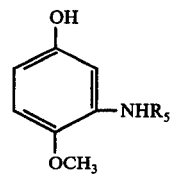

wherein $R_5$ has the meaning given above or on a salt of said compound formed with a mineral or organic acid, on a member selected from the group consisting of (a) a compound of the formula

wherein Z, $R_1$, $R_2$, $R_3$ and $R_4$ have the meanings given above, or a salt of said compound, the molar ratio of compounds III/II being preferably between 0.75–1.75, the condensation being carried out at a temperature between 5°–40° C at atmospheric pressure;

(b) a benzoquinone-monoimine or diimine of the formula:

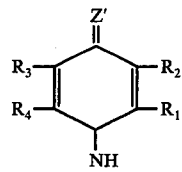

wherein Z' represents a member selected from the group consisting of oxygen or imine and $R_1$, $R_2$, $R_3$ and $R_4$ have the meanings given above the proviso that at least two of $R_1$, $R_2$, $R_3$ and $R_4$ and other than hydrogen. The condensation is carried out, preferably, at a temperature between 5°–40° C. at atmospheric pressure. The molar ratio of compounds IV/II is preferably equal to 1; and (c) a nitroso derivative of the formula:

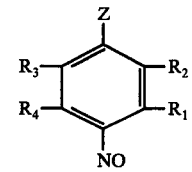

or a salt thereof, wherein Z, $R_1$, $R_2$, $R_3$ and $R_4$ have the meanings given above, the condensation being carried out, preferably, at a temperature between 15°–80° C. at atmospheric pressure, the molar ratio of compounds V/II being between 1–1.5.

The condensation of compounds III or IV on compound II is carried out in an aqueous, hydroacetonic or hydroalcoholic medium at a pH made alkaline by the addition thereto of, for example, ammonia, and in the presence of a large excess of $H_2O_2$ (10–75% $H_2O_2$ – 20 volumes), compounds III, IV and II generally being used in equimolar amounts.

The condensation of compound V on compound II is carried out in an aqueous, hydroalcoholic (the proportion of alcohol varying between 0–100%) or hydroacetonic (the proportion of acetone being between 0–50%) medium, or even in absolute ethyl alcohol, especially when compound I is isolated in salt form. Compounds V and II are preferably employed in equimolar amounts and the pH of the reaction medium can either be made alkaline by the addition thereto of ammonia, or made slightly acid by the addition thereto of acetic acid. It will be noted that the reaction medium itself is acidic when the compound used is a hydrochloride, hydrobromide or sulfate of compound V and thus the addition of acid to the reaction medium in this case would generally be superfluous.

The condensation of compound V on compound II is generally carried out in the presence of $H_2O_2$. However, the presence of $H_2O_2$ is not necessary in certain instances, particularly when the reaction is carried out in absolute ethyl alcohol and when the compound V utilized is in the form of a salt thereof. The amount of $H_2O_2$ (20 volumes) employed can vary between 0–75 percent by weight of the reaction mixture.

When compound I carries a quaternizable tertiary amine function the quaternary amine of this compound can be prepared by reacting it with an alkylating agent such as methyl or ethyl sulfate, methyl or ethyl iodide or bromide, or benzylchloride. The quaternization reaction can be carried out at ambient temperature in an appropriate solvent such as dioxane or a mixture of dioxane and ethanol.

The compounds of the present invention are usefully employed as dyes which exhibit good affinity for keratinic fibers, particularly human hair.

It is known, for instance, that many dyes for coloring hair often impart to the same a reddish glint or hue which is not always desirable. The present invention however provides a solution to this problem. The diamino benzoquinones of the present invention impart to keratinic fibers a wide range of green glints which diminish or suppress the red glints or highlights of conventional colorations, particularly red hair.

Diaminobenzoquinones, generally, are already known. Thus, U.S. Pat. No. 2,267,741 and French Pat. No. 847,026 describe diamino benzo 1,4-quinone of the formula

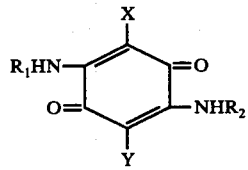

wherein X and Y can represent hydrogen; and $R_1$ and $R_2$, different from one another, can be hydrogen, alkyl or aryl. These compounds are dyes which dye wool yellow, brown or red-brown and are not suitable for the present purposes.

German Pat. No. 300,706 describes some monoaryl and diaryl aminoquinones which dye wool yellow or brown. These compounds also are not suitable for the present purposes.

French Pat. No. 1,554,772 describes aminoquinones that are used as antioxidants for a lubricant, rubber and plastic material.

The present invention also relates to a new industrial product comprising a dye composition for keratinic fibers, particularly human hair, comprising a solution of at least one compound of formula I or a salt thereof or a quaternary ammonium derivative thereof.

The compositions of the present invention are aqueous solutions which can also include one or more low molecular weight alcohols, such as ethanol or isopropanol, or one or more glycols, such as butylglycol or propylene glycol, so as to facilitate the dissolution of the dye in the water. The amount of alcohol can vary, for instance, between about 5–70 weight percent of the composition while the amount of glycol can vary generally between about 2–5 weight percent of said composition.

The concentration of the compounds of formula I, or their salts, in the dye compositions of this invention can range between about 0.005–0.5, and preferably between about 0.005–0.25, percent by weight of said composition.

The pH of the compositions of this invention can vary between about 4–11, the compounds of formula I and their salts, exhibiting strong dyeing power in this extensive pH range. The pH of the compositions can be adjusted to the desired value by the addition thereto of pH adjusting agents conventionally employed in cosmetic compositions such as, for instance, an acid including for example orthophosphoric acid, lactic acid or acetic acid, or a base such as ammonia or triethanolamine.

The compositions of the present invention can include as the dye component only the compounds of formula I, or salts thereof, in which case they provide a wide range of very luminous green solutions rich in metallic glints, ranging from silvery almond green to very dark green, passing through light bronze, ash blonds and linden colors with golden glints.

The compositions of the present invention can, however, include other direct dyes, for example, azo dyes, anthraquinone dyes, nitro dyes of the benzene series, indophenols, indoanilines, indamines or oxazines. The present composition can also include oxidation dyes such as di- or tri-amino phenols or amino diphenols.

Further, the compositions of the present invention can also include adjuvants conventionally employed in cosmetic compositions such as wetting agents, emollients or perfumes. The compositions can also be packaged under pressure in aerosol containers with a conventional liquefied aerosol propellant such as a fluorinated hydrocarbon including dichlorodifluoromethane, trichloromonofluoromethane and mixtures thereof, and other halogeneted hydrocarbons.

The compositions of the present invention, in one embodiment, can be employed to provide durable hair colorations. In this embodiment the compositions are applied to the hair for a period ranging from about 10–30 minutes, the thus-treated hair thereafter being rinsed, washed and dried.

The present compositions can also be employed as a hair rinse lotion for use in imparting to the hair a slight coloration. In this embodiment the compositions are applied to washed hair, which application is not followed by any rinsing operation.

Further, the compositions of the present invention can be used as a hair setting lotion to impart a slight coloration to the hair and to improve the holding power of the set. In this embodiment, the compositions comprise a hydroalcoholic solution of the dye component in combination with at least one cosmetic film-forming resin. The hair setting lotion is applied to previously washed and rinsed wet hair, followed by rolling the hair up on curlers and drying the hair.

Representative cosmetic film-forming resins usefully employed in the hair setting lotions of this invention include polyvinylpyrrolidone, having a molecular weight between 40,000 and 400,000; copolymers of vinylpyrrolidone and vinyl acetate (70–30:30–70%); copolymers of vinyl acetate and an unsaturated carboxylic acid such as crotonic acid (90:10) having a molecular weight of about 20,000–50,000; copolymers resulting from the copolymerization of vinyl acetate (75–85%), crotonic acid (5–18%) and an acrylic or methacrylic ester (5–15%), copolymers resulting from the copolymerization of vinyl acetate and an alkyl vinyl ether, copolymers resulting from the copolymerization of vinyl acetate (63–88%), crotonic acid (5–15%) and a vinyl ester (5–25%) of a long carbon chain acid (10–22 carbon atoms) or an allyl or methallyl ester of a long carbon chain acid (10–22 carbon atoms), copolymers resulting from the copolymerization of 65–80% ester of an unsaturated alcohol (2–12 carbon atoms) and a short carbon chain acid (2–5 carbon atoms) or a 7–12% unsaturated short chain acid (4–20 carbon atoms) and 10–20% at least one ester of a saturated short chain alcohol (8–18 carbon atoms) and an unsaturated acid (4–20 carbon atoms) and copolymers resulting from the copolymerization of at least one unsaturated ester at at least one unsaturated acid.

The preferred cosmetic film forming resins include polyvinylpyrrolidone, copolymers of crotonic acid and vinyl acetate, copolymers of vinylpyrrolidone and vinyl acetate, copolymers of maleic anhydride and butyl vinyl ether, terpolymers of methyl methacrylate-stearyl methacrylatedimethyl methacrylate; and terpolymers of vinyl acetate-allyl stearate and allyloxy-acetic acid.

The cosmetic film forming resin is generally present in amounts of about 1–3 percent by weight of the total composition.

The alcohols conveniently employed to produce the hair setting lotions according to the present invention are low molecular weight alcohols, preferably, ethanol or isopropanol, which are present in amounts generally of about 20–70 percent by weight of said composition.

The following examples are given to illustrate the invention. In the examples an ethyl alcohol at 96° corresponds to 950.189 g/kg of alcohol.

EXAMPLE 1

Preparation of 2-amino-5-(2'-methoxy-4'-amino anilino)-1,4-benzoquinone of the formula:

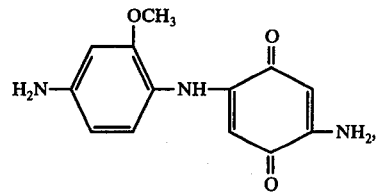

0.02 mole (2.78g) of 3-amino-4-methoxy phenol is dissolved in 200 cc of water to which has been added 20 cc of ammonia (22° Be) and 50 cc of $H_2O_2$ (20 volumes). As soon as this solution has been prepared, there is added, with agitation, a solution of 0.02 (4.27g) of methoxyparaphenylenediamine sulfate in 200 cc of water. After 4 hours of agitation, the reaction mixture is filtered and the resulting 2-amino-5-(2'-methoxy-4'-amino anilino)-1,4-benzoquinone is washed with water. The raw product is then recrystallized in a mixture of dimethyl formamide and water and dried under a vacuum with a boiling water bath for 8 hours. The product exhibits a melting point of 267° C.

| Analysis | Calculated For $C_{13}H_{13}N_3O_3$ | Found | |
|---|---|---|---|
| C% | 60.22 | 59.68 | 59.82 |
| H% | 5.05 | 5.11 | 5.08 |
| N% | 16.21 | 16.33 | 16.12 |

EXAMPLE 2

Preparation of 2-amino-5-(4'-dimethylamino anilino)-1,4-benzoquinone of the formula:

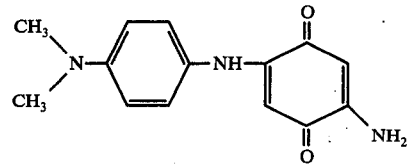

0.1 mole (13.9g) of 3-amino-4-methoxy phenol is dissolved in 250 cc of water to which has been added 50 cc of ammonia (22° Be). To this solution there are initially added 500 cc of $H_2O_2$ (20 volumes) and then, immediately thereafter, and with agitation, 0.1 mol (20.9g) of N,N-dimethylparaphenylene diamine dihydrochloride in 250 cc of water. The reaction mixture is left to stand for 8 hours at ambient temperature, at which time it is filtered to recover said 2-amino-5-(4'-dimethylamino anilino)-1,4-benzoquinone. This raw product, after being washed with water, is recrystallized in dimethylformamide and dried under a vacuum with a boiling water bath for 5 hours. The product exhibits a melting point of 300° C.

| Analysis | Calculated For $C_{14}H_{15}N_3O_2$ | Found | |
|---|---|---|---|
| C% | 65.35 | 65.17 | 65.22 |
| H% | 5.88 | 6.01 | 5.79 |
| N% | 16.33 | 16.35 | 16.27 |

EXAMPLE 3

Preparation of 2-amino-5-(2'-methoxy-3',5'-dimethyl-4'-amino anilino)-1,4-benzoquinone of the formula

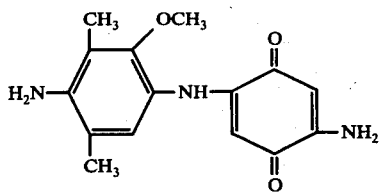

0.01 mole (1.39 g) of 3-amino-4-methoxy phenol is dissolved in 30 cc of water to which has been added 8cc of ammonia (22° Be). To this solution there are added 50 cc of $H_2O_2$ (20 volumes) and immediately thereafter, with good agitation, 0.01 mole (1.64 g) of 2,6-dimethyl-3-methoxy-1,4-benzoquinone-diimine. After agitating the resulting mixture for about twenty minutes, the same is filtered to recover the above 2-amino-5-(2'-methoxy-3',5'-dimethyl-4'-amino anilino)-1,4-benzoquinone which is then washed with water. After recrystallizing the same in a mixture of dimethylformamide and water and drying for five hours under a vacuum with a boiling water bath, the product exhibits a melting point of 214° C.

| Analysis | Calculated For $C_{15}H_{17}O_3N_3$ | Found | |
|---|---|---|---|
| C% | 62.70 | 62.53 | 62.61 |
| H% | 5.96 | 5.96 | 6.14 |
| N% | 14.63 | 14.55 | 14.43 |

EXAMPLE 4

Preparation of 2-amino-5-(2'-methoxy-5'-methyl-4'-amino anilino)-1,4-benzoquinone of the formula

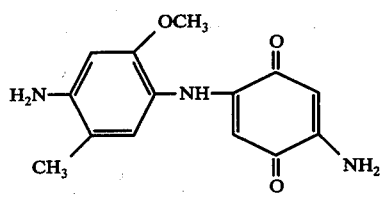

0.01 mole (1.39 g) of 3-amino-4-methoxy phenol is dissolved in 20 cc of water to which has been added 10 cc of ammonia (22° Be) and 100 cc of $H_2O_2$ (20 volumes). As soon as this solution has been prepared there is added, with good agitation, 0.01 mole (1.60 g) of 2-methyl-5-methoxy-1,4-benzoquinone diimine. After a 30 minute reaction period, the reaction mixture is filtered to recover the expected 2-amino-5-(2'-methoxy-5'-methyl-4'-amino anilino)-1,4-benzoquinone which is then washed with water. The raw product is then recrystallized in a mixture of dimethylformamide and water and dried for 6 hours under a vacuum with a boiling water bath. The product exhibits a melting point of 273° C.

Molecular mass calculated for $C_{14}H_{15}O_3N_3 = 273$

Molecular mass found by potentiometric dosage in acetic acid with perchloric acid = 284

| Analysis | Calculated For $C_{14}H_{15}O_3N_3$ | Found | |
|---|---|---|---|
| C% | 61.53 | 61.21 | 61.36 |
| H% | 5.53 | 5.60 | 5.67 |
| N% | 15.38 | 15.55 | 15.27 |

EXAMPLE 5

Preparation of 2-amino-5-(4'-di-β-hydroxyethylamino anilino)-1,4-benzoquinone of the formula

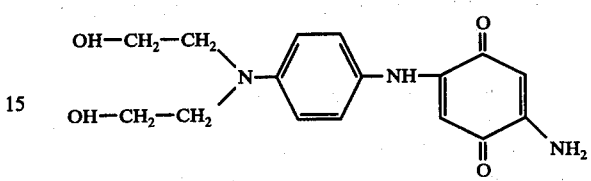

0.01 mole (1.39 g) of 3-amino-4-methoxy phenol is dissolved in 15 cc of water, 3 cc of acetic acid and 75 cc of $H_2O_2$ (20 volumes). As soon as this solution is prepared there is added, with good agitation, a solution of 0.01 mole (2.1 g) of 4-nitroso-N,N-di-β-hydroxyethyl aniline in 30 cc of a 50% aqueous ethanol solution. After agitating the resulting reaction mixture for two hours, the same is filtered to recover the expected 2-amino-5-(4'-di-β-hydroxyethylamino anilino)-1,4-benzoquinone, which is then washed with water. The product, after recrystallization in a mixture of dimethylformamide and water and drying for 10 hours under a vacuum with a boiling water bath, exhibits a melting point of 199° C.

| Analysis | Calculated For $C_{16}H_{19}N_3O_4$ | Found | |
|---|---|---|---|
| C% | 60.55 | 60.62 | 60.62 |
| H% | 6.04 | 5.95 | 6.17 |
| N% | 13.24 | 13.47 | 13.20 |

EXAMPLE 6

Preparation of 2-N-β-hydroxyethylamino-5-(2'-methoxy-3',5'-dimethyl-4'-amino anilino)-1,4-benzoquinone of the formula

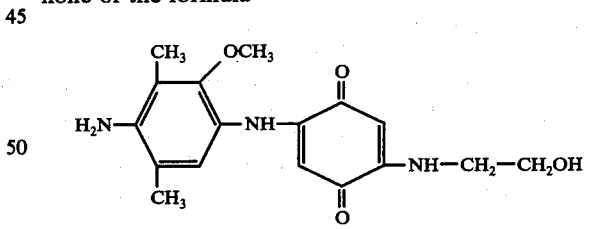

0.02 mole (3.66 g) of 3-N-β-hydroxyethylamino-4-methoxy phenol is dissolved in 30 cc of water, 16 cc of ammonia (22° Be) and 100 cc of $H_2O_2$ (20 volumes). As soon as this solution has been prepared there is added thereto, with agitation, 0.02 mole (3.28 g) of 2-methoxy-3,5-dimethyl-1,4-benzoquinonediimine. The resulting reaction mixture is agitated for 45 minutes at which time it is filtered to recover the 2-N-β-hydroxyethylamino-5-(2'-methoxy-3',5'-dimethyl-4'-amino anilino)-1,4-benzoquinone which is then washed with water. After recrystallizing the same in a mixture of dimethylformamide and water and drying under a vacuum with a boiling water bath for 8 hours, the product exhibited a melting point of 187° C.

| Analysis | Calculated For $C_{17}H_{21}O_4N_3$ | Found | |
|---|---|---|---|
| C% | 61.63 | 61.27 | 61.32 |
| H% | 6.34 | 6.22 | 6.28 |
| N% | 12.68 | 12.57 | 12.82 |

EXAMPLE 7

Preparation of 2-amino-5-[4'-(N-ethyl,N-β-piperidinoethyl)amino anilino]-1,4-benzoquinone of the formula:

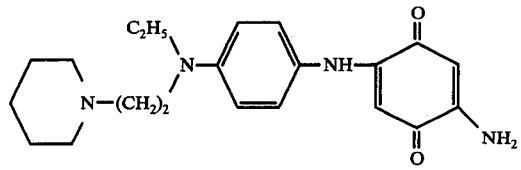

To a solution of 0.04 mole (5.36 g) of 3-amino-4-methoxy phenol in 50 cc of water to which has been added 10 cc of ammonia (22° Be) and 200 cc of $H_2O_2$ (20 volumes) there is added, with good agitation, 0.04 mole (13.3g) of 4-nitroso-N-ethyl,N-β-piperidinoethyl aniline dihydrochloride in 50 cc of water. The resulting reaction mixture is agitated for a period of two hours at which time it is filtered to recover 2-amino-5-[4'-(N-ethyl,N-β-piperidinoethyl)amino anilino]-1,4-benzoquinone which is then washed with boiling water. This product, after recrystallization in a mixture of dimethylformamide and water and drying for 8 hours under vacuum with a boiling water bath, exhibits a melting point of 110° C.

Molecular mass calculated for $C_{21}H_{28}N_4O_2 = 368$
Molecular mass found by potentiometric dosage in acetic acid by perchloric acid = 376

| Analysis | Calculated For $C_{21}H_{28}N_4O_2$ | Found | |
|---|---|---|---|
| C% | 68.45 | 68.45 | 68.40 |
| H% | 7.66 | 7.69 | 7.46 |
| N% | 15.21 | 14.98 | 15.17 |

EXAMPLE 8

Preparation of 2-amino-5-[4'-N-(ethyl,β-N-methyl-piperidinium-ethyl)amino anilino]-1,4-benzoquinone iodide of the formula:

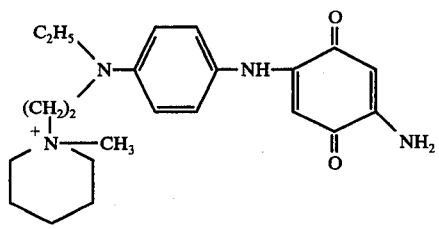

0.0027 mole (1 g) of the compound of Example 7 is dissolved in 7 cc of absolute ethyl alcohol and 20 cc of dioxane. To this solution maintained at 40° C there are added, little by little, 3 cc of methyl iodide. The resulting reaction mixture is left to stand for one hour at 40° C at which time it is filtered to recover 1.3 g of the above quatenary salt which exhibits a melting point of 265° C.

| Analysis | Calculated for $C_{22}H_{31}N_4O_2I$ | Found | |
|---|---|---|---|
| C% | 51.76 | 51.56 | 51.34 |
| H% | 6.08 | 6.16 | 6.14 |
| N% | 10.99 | 10.88 | 11.15 |
| I% | 24.90 | 25.00 | |

EXAMPLE 9

Preparation of 2-N-β-hydroxyethylamino-5-(2'-methoxy-4'-amino anilino)-1,4-benzoquinone of the formula:

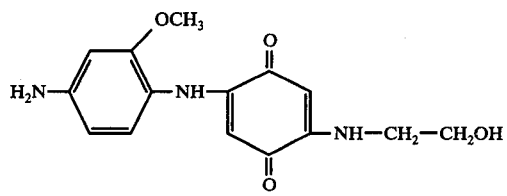

To a solution of 0.01 mole (1.83 g) of 3-N-β-hydroxyethylamino-4-methoxy phenol in 25 cc of water to which has been added 10 cc of ammonia (22° Be) and 100 cc of $H_2O_2$ (20 volumes) there is added, with good agitation, 0.01 mole (2.10 g) of methoxyparaphenylenediamine dihydrochloride in 25 cc of water. The resulting reaction mixture is agitated for two hours at which time it is filtered to recover 2-N-β-hydroxyethylamino-5-(2'-methoxy-4'-amino anilino)-1,4-benzoquinone which is then washed with water. After recrystallizing the same in a mixture of dimethyl formamide and water and drying under a vacuum with a boiling water bath for six hours, the product exhibited a melting point of 215° C.

| Analysis | Calculated For $C_{15}H_{17}N_3O_4$ | Found | |
|---|---|---|---|
| C% | 59.39 | 59.14 | 59.17 |
| H% | 5.65 | 5.73 | 5.78 |
| N% | 13.86 | 14.02 | 13.88 |

EXAMPLE 10

Preparation of 2-N-β-hydroxyethylamino-5-[4'-(N-ethyl,N-β-piperidinoethyl)amino anilino]-1,4-benzoquinone dihydrochloride of the formula:

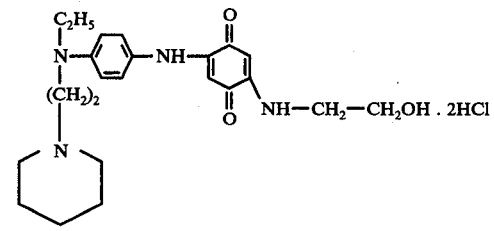

There are heated for 45 minutes with a boiling water bath, 0.01 mole (3,33 g) of 4-nitroso-N,N-ethyl,β-piperidinoethyl anilidine dihydrochloride and 0.01 mole (1.83 g) of 3-N-β-hydroxyethylamino-4-methoxy phenol in 20 cc of absolute ethyl alcohol. After filtering the boiling reaction mixture, the resulting filtrate is cooled to 0° C. for a few hours at which time the cooled filtrate is filtered to recover 2-N-β-hydroxyethyl-amino-5-[4'-(N-ethyl,N-β-piperidinoethyl)amino anilino]-1,4-benzoquinone dihydrochloride, which is washed with ethanol and then with acetone. The product is chromatographically pure and melts at 226° C.

| Analysis | Calculated For $C_{23}H_{32}O_3N_4 2HCl \cdot H_2O$ | Found |
|---|---|---|
| Cl% | 14.11 | 13.97 |

EXAMPLE 11

Preparation of 2-N-β-hydroxyethylamino-5-[4'-(di-β-hydroxyethylamino)anilino]-1,4-benzoquinone of the formula:

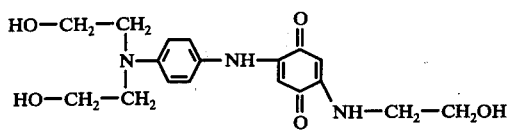

0.01 mole (1.83 g) of 3-N-β-hydroxyethylamino-4-methoxy phenol is dissolved in 30 cc of acetone and 100 cc of $H_2O_2$ (20 volumes). As soon as this solution has been prepared there is added, with good agitation, 0.01 mole (2.46 g) of 4-nitroso-N-β-hydroxyethylaniline hydrochloride. The resulting reaction mixture is continued to be agitated for one hour at which time there are added thereto 10 cc of ammonia (22° Be) to precipitate the 2-N-β-hydroxyethylamino-5-[4'-(di-β-hydroxyethylamino)anilino]-1,4-benzoquinone. This precipitate, after being filtered and washed with water, is chromatographically pure. After drying for 5 days under a vacuum at ambient temperature, the product exhibited a melting point of 164° C.

Molecular mass calculated for $C_{18}H_{23}O_5N_3 = 361$

Molecular mass found by potentiometric dosage in acetic acid with perchloric acid = 366

| Analysis | Calculated For $C_{18}H_{23}N_3O_5$ | Found | |
|---|---|---|---|
| C% | 59.82 | 59.28 | 59.17 |
| H% | 6.42 | 6.27 | 6.32 |
| N% | 11.62 | 11.49 | 11.56 |

EXAMPLE 12

Preparation of 2-amino-5-(3'-chloro-4'-hydroxy anilino)-1,4-benzoquinone of the formula:

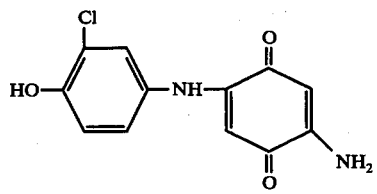

0.02 mole (2.78 g) of 3-amino-4-hydroxy phenol is dissolved in 200 cc of water to which have been added 20 cc of ammonia (22° Be). To this solution there are initially added 100 cc of $H_2O_2$ (20 volumes) and the immediately thereafter, with good agitation, 0.02 mole (3.60 g) of 2-chloro-4-amino phenol hydrochloride in 200 cc of water. The reaction mixture is left to stand for 5 hours at ambient temperature at which time it is filtered to recover the 2-amino-5-(3'-chloro-4'-hydroxyanilino)-1,4-benzoquinone which is then washed with water, recrystallized in a mixture of dimethylformamide and water and dried for 5 hours under a vacuum with a boiling water bath. The product is chromatographically pure.

| Analysis | Calculated For $C_{12}H_9O_3N_2Cl$ | Found | |
|---|---|---|---|
| C% | 54.44 | 54.07 | 54.12 |
| H% | 3.40 | 3.52 | 3.67 |
| N% | 10.58 | 10.36 | 10.30 |
| Cl% | 13.42 | 13.18 | 13.26 |

EXAMPLE 13

Preparation of 2-amino-5-(4'-hydroxy-2',3'-dimethyl anilino)-1,4-benzoquinone of the formula:

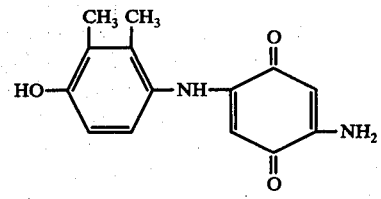

0.01 mole (1.39 g) of 3-amino-4-methoxy phenol is dissolved in 100 cc of water to which have been added 50 cc of acetone and 10 cc of ammonia (22° Be). To this solution there are added 100 cc of $H_2O_2$ (20 volumes) and immediately thereafter, with good agitation, 0.01 mole (1.37 g) of 2,3-dimethyl-4-amino phenol in suspension in 100 cc of water. The resulting reaction mixture is agitated for three hours at which time it is filtered to recover the 2-amino-5-(4'-hydroxy-2',3'-dimethyl anilino)-1,4-benzoquinone which is first washed with water and then with acetone. It is dried for 8 hours under a vacuum with a boiling water bath and is chromatographically pure, melting at 320° C.

| Analysis | Calculated For $C_{14}H_{14}N_2O_3$ | Found | |
|---|---|---|---|
| C% | 65.10 | 64.92 | 64.87 |
| H% | 5.46 | 5.52 | 5.57 |
| N% | 10.85 | 10.77 | 10.69 |

EXAMPLE 14

Preparation of 2-N-β-hydroxyethylamino-5-(2',5'-dimethyl-4'-hydroxy anilino)-1,4-benzoquinone of the formula:

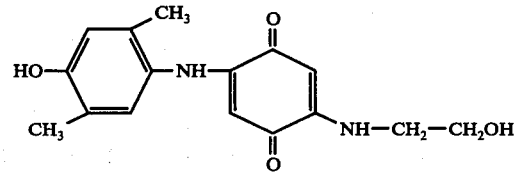

0.02 mole (3.60 g) of 3-β-hydroxyethylamino-4-methoxy phenol is dissolved in 30 cc of acetone to which have been added 2 cc of ammonia (22° Be) and 150 cc of $H_2O_2$ (20 volumes). As soon as this solution has been prepared there is added, at ambient temperature and with good agitation, 0.02 mole (3.02g) of 2,5-dimethyl-4-nitroso phenol in 20 cc of acetone. The resulting reaction mixture is agitated for 5 hours at 35° C at which time it is filtered to recover said 2-N-β-hydroxyethylamino-5-(2',5'-dimethyl-4'-hydroxy anilino)-1,4-benzoquinone which is washed with water and with acetone. After recrystallizing it in a mixture of dimethylformamide and water it exhibits a melting point of 249° C.

| Analysis | Calculated For C₁₆H₁₈O₄N₂ | Found | |
|---|---|---|---|
| C% | 63.57 | 63.62 | 63.57 |
| H% | 5.96 | 6.01 | 6.01 |
| N% | 9.27 | 9.18 | 9.12 |

EXAMPLE 15

Preparation of 2-N-β-diethylaminoethylamino-5-(4'-N,N-di-β-hydroxyethylamino anilino)-1,4-benzoquinone of the formula:

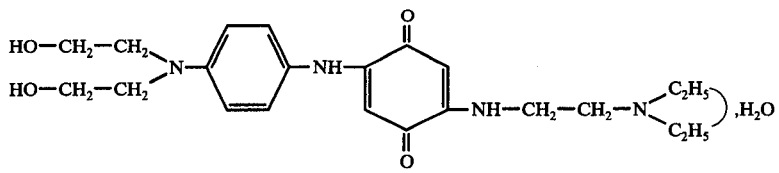

0.01 mole (2.75 g) of 3-N-β-diethylaminoethylamino-4-methoxy phenol hydrochloride is dissolved in 50 cc of acetone, 100 cc of H₂O₂ (20 volumes) and 5 cc of ammonia (22° Be). As soon as this solution has been prepared there is added thereto, with agitation, 0.01 mole (2.46 g) of 4-nitroso-N,N-di-β-hydroxyethyl aniline hydrochloride. The resulting reaction mixture is agitated for one hour at which time there is added thereto 5 cc of ammonia (22° Be). The reaction mixture is then filtered to recover said 2-N-β-diethylaminoethylamino-5-(4'-N,N-di-β-hydroxyethylamino anilino)-1,4-benzoquinone which is then washed with water. The product is chromatographically pure and after drying for 5 days under a vacuum at ambient temperature it exhibits a melting point of 120° C.

| Analysis | Calculated For C₂₂H₃₂N₄O₄·H₂O | Found | |
|---|---|---|---|
| C% | 60.82 | 60.62 | 60.92 |
| H% | 7.83 | 7.65 | 7.70 |
| H% | 12.90 | 12.94 | 12.73 |

EXAMPLE 16

Preparation of 2-N-β-(methyl, diethylammonium) ethylamino-5-(4'-N,N-di-β-hydroxyethylamino anilino)-1,4-benzoquinone iodide of the formula:

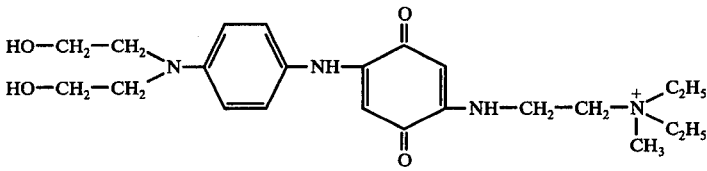

0.0023 mole (1g) of the compound of Example 15 is dissolved in 7 cc of absolute ethanol and 20 cc of diox-ane. To this solution, at ambient temperature and with agitation, there are added, little by little, 3 cc of methyl iodide. The resulting reaction mixture is agitated for 8 hours at which time it is filtered to recover 1.18 g of the above quaternary salt which is then washed with a little dioxane and finally with sulfuric ether. It melts at 243° C.

| Analysis | Calculated For C₂₃H₃₅N₄O₄I | Found | |
|---|---|---|---|
| C% | 49.46 | 49.12 | 49.19 |
| H% | 6.29 | 6.27 | 6.31 |
| N% | 10.03 | 10.00 | 9.80 |
| I% | 22.75 | 22.60 | |

EXAMPLE 17

Preparation of 2-β-aminoethylamino-5-(2'-methoxy-3',5'-dimethyl-4'-amino anilino)-1,4-benzoquinone of the formula:

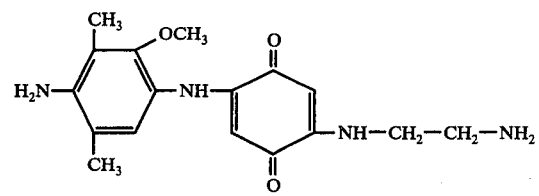

0.01 mole (2.63 g) of 3-β-aminoethylamino-4-methoxy phenol monohydrobromide is dissolved in 20 cc of water and 100 cc of H₂O₂ (20 volumes). As soon as this solution has been prepared and cooled in ice, there is added, with agitation, 0.01 mole (1.64 g) of 2,6-dimethyl-3-methoxy-1,4-benzoquinonediimine. The resulting reaction mixture is agitated for a period of about 20 minutes at which time it is alkalinized to a pH of about 10 by the addition thereto of ammonia (22° Be). The reaction mixture is then filtered to recover the 2-β-aminoethylamino-5-(2'-methoxy-3',5'-dimethyl-4'-amino anilino)-1,4-benzoquinone which is then washed with water. After recrystallizing the same in a mixture of acetone and water and drying for several days under a vacuum at ambient temperature, the product exhibits a melting point of 96° C and is chromatographically pure.

Molecular mass calculated for $C_{17}H_{22}O_3N_4 = 330$

Molecular mass found by potentiometric dosage in acetic acid with perchloric acid $= 348$

EXAMPLE 18

Preparation of 2-N-β-hydroxyethylamino-5-[2'-methyl-4'-(N-ethyl,N-β-mesylaminoethyl)amino anilino]-1,4-benzoquinone of the formula:

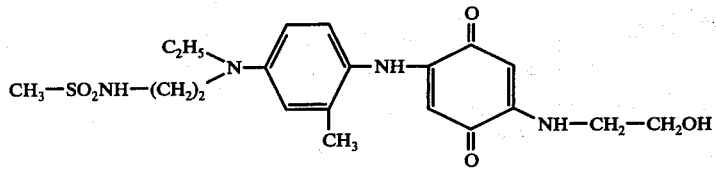

0.01 mole (1.83 g) of 3-N-β-hydroxyethlamino-4-methoxy phenol is dissolved in 50 cc of a 50% hydroacetonic solution. To this solution there are added 25 cc of ammonia (22° Be) and 100 cc of $H_2O_2$ (20 volumes) and then, little by little, with agitation and while maintaining the temperature thereof at about 10° C, a solution of 0.01 mole (4.36 g) of N-ethyl-N-β-mesylaminoethyl paratoluene diamine sulfate monohydrate in 20 cc of water. The resulting reaction mixture is agitated for one hour at which time it is filtered to recover the precipitate which has formed, which precipitate is the above product. The precipitate is washed with water, recrystallized twice in a mixture of dimethylformamide and water and dried under a vacuum at 80° C. The product exhibits a melting point of 158° C.

| Analysis | Calculated For $C_{20}H_{28}N_4O_5S$ | Found | |
|---|---|---|---|
| C% | 55.04 | 54.68 | 54.72 |
| H% | 6.41 | 6.39 | 6.32 |
| N% | 12.84 | 13.00 | 13.03 |
| S% | 7.34 | 7.30 | 7.27 |

EXAMPLE 19

Preparation of 2-N-β-hydroxyethylamino-5-[(4'-N-ethyl,N-β-acetylaminoethyl)amino anilino]-1,4-benzoquinone of the formula:

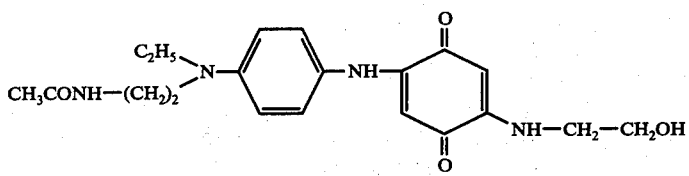

To a solution of 0.05 mole (9.2 g) of 3-N-β-hydroxyethylamino-4-methoxy phenol in 200 cc of water to which has been added 5 cc of ammonia (22° Be) and 500 cc of $H_2O_2$ (20 volumes), there is added, with good agitation, a solution of 0.05 mole (11.7 g) of 4-nitroso-N,ethyl,N-acetylamino-ethylaniline in 200 cc of acetone. When the temperature of the reaction mixture reaches 35° C, the same is then cooled with ice. Agitation of the reaction mixture is continued for a period of two hours at which time the same is filtered to recover the precipitate which has formed, said precipitate being the above-identified product. The precipitate is washed and recrystallized twice with the aid of ethyl acetate. The resulting product exhibits a melting point of 164° C.

| Analysis | Calculated For $C_{20}H_{26}N_4O_4$ | Found | |
|---|---|---|---|
| C% | 62.16 | 61.81 | 61.97 |
| H% | 6.78 | 6.57 | 6.84 |
| N% | 14.50 | 14.72 | 14.59 |

EXAMPLE 20

Preparation of 2-N-β-hydroxyethylamino-5-[2'-chloro-4'-N,N-diethylamino anilino]-1,4-benzoquinone of the formula:

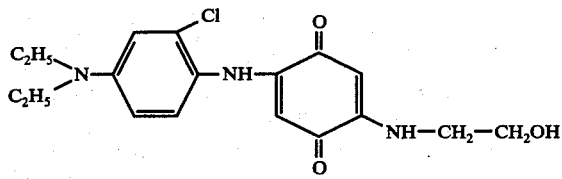

To a solution of 0.02 mole (3.66 g) of 3-N-β-hydroxyethylamino-4-methoxy phenol in 40 cc of water to which has been added 200 cc of $H_2O_2$ (20 volumes) and 2 cc of ammonia (22° Be), there is added, with good agitation, a solution of 0.02 mole (4.24 g) of 3-chloro-4-nitroso-N,N-diethyl aniline in 100 cc of acetone. The resulting reaction mixture is agitated for two hours at which time it is filtered to recover the precipitate which has formed, said precipitate being the above product. The precipitate is then carefully washed with warm water and after recrystallization in a mixture of dimethylformamide and water and two recrystallizations of methylisobutyl ketone, the product exhibits a melting point of 158° C.

Molecular mass calculated for $C_{18}H_{22}N_3O_3Cl = 363.5$

Molecular mass found by potentiometric dosage in acetic acid with perchloric acid = 369

EXAMPLE 21

Preparation of 2-N-β-hydroxyethylamino-5-[4'-N(ethyl, β-piperidinoethyl)amino anilino]-1,4-benzoquinone of the formula:

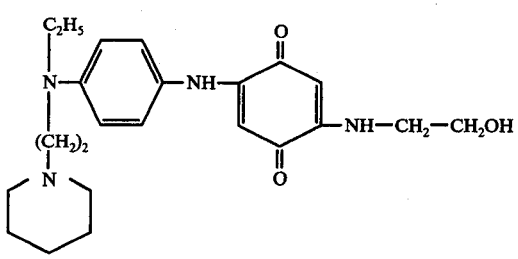

2.9 g of 2-N-β-hydroxyethylamino-5-[4'-N(ethyl,β-piperidinoethyl)amino anilino]-1,4-benzoquinone are dissolved in 100 cc of water. The same is alkalinized to a pH of 8 by the addition thereto of ammonia (22° Be). The reaction mixture is then filtered to recover the precipitate which has formed, which precipitate is the above product, is then washed with water and, after recrystallization in a mixture of dimethyl formamide and water and drying under a vacuum at 80° C, exhibits a melting point of 174° C.

| Analysis | Calculated For $C_{23}H_{32}N_4O_3$ | Found | |
|---|---|---|---|
| C% | 66.96 | 66.73 | 67.18 |
| H% | 7.82 | 7.79 | 7.72 |
| N% | 13.58 | 13.69 | 13.70 |

EXAMPLE 22

Preparation of 2-N-β-hydroxyethylamino-5[4'-[N-ethyl,β-(methyl piperidinium)ethyl]-amino anilino]-1,4-benzoquinone iodide of the formula:

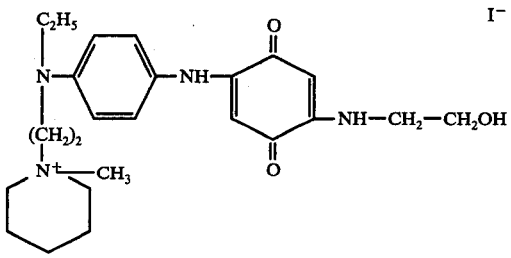

0.0118 mole (5 g) of 2-N-β-hydroxyethylamino-5-[4'-N(ethyl,β-piperidinoethyl)amino anilino]-1,4-benzoquinone, prepared in accordance with the method set forth in Example 21, is dissolved in 35 cc of ethanol to which has been added 100 cc of dioxane. To this solution, maintained at a temperature of 40° C, there are added, little by little, 20 cc of methyl iodide. The resulting reaction mixture is left to stand for 12 hours at ambient temperature at which time it is filtered to recover the above quaternary salt which is first washed with dioxane and then with ether. The product exhibits a melting point of 136° C.

| Analysis | Calculated For $C_{24}H_{35}N_4O_3I$ | Found |
|---|---|---|
| I% | 22.90 | 22.96 |

EXAMPLE 23

Preparation of 2-N-β-hydroxyethylamino-5-[4'-(dimethylamino)anilino]-1,4-benzoquinone of the formula:

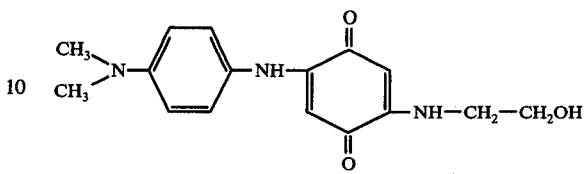

There are introduced into 25 cc of absolute ethanol, (a) 0.016 mole (3 g) of 4-nitroso dimethyl aniline hydrochloride, and (b) 0.011 mole (2 g) of 3-N-β-hydroxyethylamino-4-methoxy phenol. The resulting reaction mixture is heated to reflux, with agitation, for one hour at which time it is filtered to recover the precipitate which has formed. The precipitate is then washed with ethanol and treated with 100 cc of an aqueous ammonia solution (11.5° Be) with agitation, for about 30 minutes. The reaction mixture is then filtered to recover the 2-N-β-hydroxyethylamino-5-[4'-(dimethylamino)anilino]-1,4-benzoquinone which after washing with water, recrystallization in a mixture of dimethylformamide and water, and drying under a vacuum exhibits a melting point of 265° C.

| Analysis | Calculated For $C_{16}H_{19}N_3O_3$ | Found | |
|---|---|---|---|
| C% | 63.77 | 63.65 | 63.77 |
| H% | 6.36 | 6.54 | 6.50 |
| N% | 13.95 | 13.95 | 13.84 |

EXAMPLE 24

Preparation of 2-N-β-hydroxyethylamino-5-[4'-(amino) anilino]-1,4-benzoquinone of the formula:

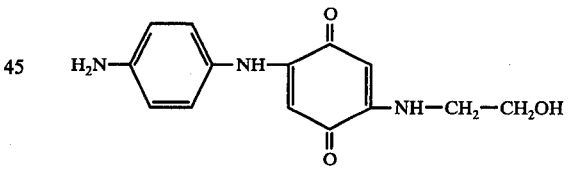

0.01 mole (1.85 g) of 3-N-β-hydroxyethylamino-4-methoxy phenol is dissolved in 25 cc of water, 25 cc of acetone, 10 cc of ammonia (22° Be) and 100 cc of $H_2O_2$ (20 volumes). To this solution there is immediately added 0.01 mole (1.81 g) of paraphenylene diamine dihydrochloride in 20 cc of water. The resulting reaction mixture is agitated for one hour at ambient temperature at which time it is filtered to recover the 2-N-β-hydroxyethylamino-5-[4'-(amino) anilino]-1,4-benzoquinone, which is washed with water and dried under a vacuum. After recrystallizing the same in a mixture of dimethylformamide and ether, the product exhibited a melting point of 248° C.

| Analysis | Calculated For $C_{14}H_{15}N_3O_3$ | Found | |
|---|---|---|---|
| C% | 61.59 | 61.04 | 61.46 |
| H% | 5.53 | 5.67 | 5.56 |

-continued

| Analysis | Calculated For $C_{14}H_{15}N_3O_3$ | Found | |
|---|---|---|---|
| N% | 15.38 | 15.50 | 15.51 |

EXAMPLE 25

Preparation of 2-amino-5-[4'-(amino)anilino]-1,4-benzoquinone of the formula:

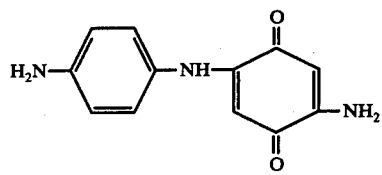

0.75 mole (10.5 g) of 3-amino-4-methoxy phenol is dissolved in 50 cc of acetone to which have been added 50 cc of ammonia (22° Be) and 250 cc of $H_2O_2$ (20 volumes). To this solution there is immediately added 0.05 mole (9.0 g) of paraphenylene diamine dihydrochloride in solution in 100 cc of water. The resulting reaction mixture is agitated for two hours at ambient temperature at which time the reaction mixture is filtered to recover the precipitate which has formed. After recrystallizing the precipitate in ethylacetate and washing the recrystallized product initially with a little methyl cellosolve and then with little ether, 2-amino-5-[4'-(amino)anilino]-1,4-benzoquinone is obtained which is chromatographically pure and which melts with decomposition above 260° C.

| Analysis | Calculated For $C_{12}H_{11}N_3O_2$ | Found | |
|---|---|---|---|
| C% | 62.87 | 63.03 | 63.07 |
| H% | 4.84 | 5.12 | 5.07 |
| N% | 18.33 | 18.23 | 18.29 |

EXAMPLE 26

Preparation of 2-N-β-hydroxyethylamino-5-[(2'-methoxy-5'-methyl-4'-amino)anilino]-1,4-benzoquinone of the formula:

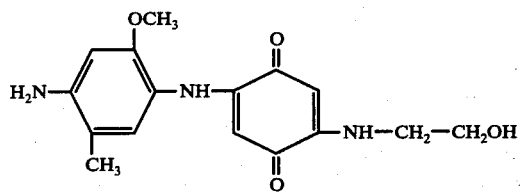

0.625 millimole (0.11 g) of 3-N-β-hydroxyethylamino-4-methoxy phenol is dissolved in 2 cc of water to which have been added 1 cc of ethanol, 0.5 cc of ammonia (22° Be) and 3 cc of $H_2O_2$ (20 volumes). As soon as this solution has been prepared there is added thereto, with agitation, 0.62 millimole (0.10 g) of 2-methyl-5-methoxy-1,4-benzoquinonediimine. The resulting reaction mixture is agitated for 15 minutes at which time it is filtered to recover said 2-N-β-hydroxyethylamino-5-[(2'-methoxy-5'-methyl-4'-amino) anilino]-1,4-benzoquinone, which is washed with water and then recrystallized in a mixture of dimethylformamide and water. After drying the same under a vacuum it exhibited a melting point of 227° C.

| Analysis | Calculated For $C_{16}H_{19}N_3O_4$ | Found | |
|---|---|---|---|
| C% | 60.55 | | 60.28 |
| H% | 6.04 | | 6.14 |
| N% | 13.24 | | 13.04 |

EXAMPLE 27

Preparation of 2-N-β-hydroxyethylamino-5-[(2',5'-dimethyl-4'-amino)anilino]-1,4-benzoquinone of the formula:

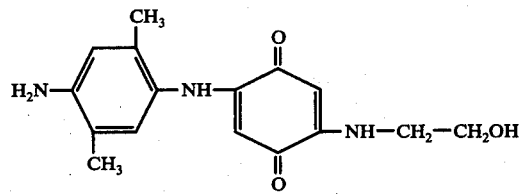

0.02 mole (3.66 g) of 3-N-β-hydroxyethylamino-4-methoxy phenol is dissolved in 50 cc of water to which have been added 20 cc of ammonia (22° Be) and 200 cc of $H_2O_2$ (20 volumes). To this solution there is immediately added, with agitation, 0.02 mole (4.18 g) of 2,5-dimethyl paraphenylene diamine dihydrochloride in 50 cc of water. The resulting reaction mixture is agitated for 1.5 hours at ambient temperature, at which time it is filtered to recover the 2-β-hydroxyethylamino-5-[(2',5'-dimethyl-4'-amino)anilino]-1,4-benzoquinone which is washed with water and recrystallized in acetone. After drying under a vacuum at 80° C the product exhibited a melting point of 248° C.

| Analysis | Calculated For $C_{16}H_{19}N_3O_3$ | Found | |
|---|---|---|---|
| C% | 63.77 | 63.35 | 63.06 |
| H% | 6.36 | 6.42 | 6.15 |
| N% | 13.95 | 14.08 | 14.10 |

EXAMPLE 28

Preparation of 2-N-β-hydroxyethylamino-5-[4'-N-(ethyl, carbamylmethyl)amino anilino]-1,4-benzoquinone of the formula:

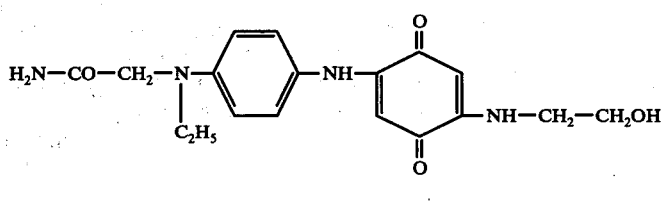

0.015 mole (2.7g) of 3-N-β-hydroxyethylamino-4-methoxy phenol is dissolved in 25 cc of water to which have been added 10 cc of acetone, 10 cc of ammonia (22° Be) and 10 ml of H₂O₂ (30 volumes). To this solution there is added, with agitation, 0.01 mole (1.93 g) of N-(ethyl,carbamylmethyl) paraphenylene diamine in 20 cc of water. The resulting reaction mixture is agitated for two hours at 30° C at which time it is filtered to recover the 2-N-β-hydroxyethylamino-5-[4'-N(ethyl, carbamylmethyl)amino anilino]-1,4-benzoquinone which is washed with water and recrystallized in a mixture of dimethylformamide and water. After drying under a vacuum at 80° C. the product exhibited a melting point of 252° C.

| Analysis | Calculated For C₁₈H₂₂N₄O₄ | Found | |
|---|---|---|---|
| C% | 60.32 | 60.00 | 60.31 |
| H% | 6.19 | 6.03 | 6.25 |
| N% | 15.63 | 15.91 | 15.75 |

EXAMPLE 29

Preparation of 2-N-β-hydroxyethylamino-5-[4'-(N-ethyl, N-β-morpholinoethyl)amino anilino]-1,4-benzoquinone of the formula:

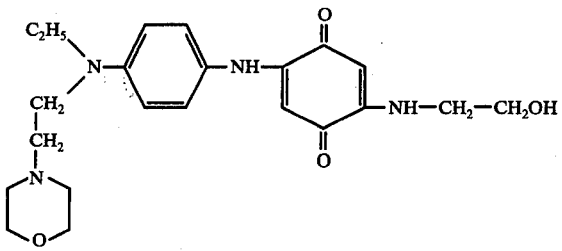

0.015 mole (2.74 g) of 3-β-hydroxyethylamino-4-methoxy phenol is dissolved in 20 cc of acetone to which have been added 10 cc of ammonia (22° Be). 50 cc of H₂O₂ (20 volumes) are added thereto and immediately thereafter, with agitation, 0.01 mole (3.36 g) of 4-nitroso-N-ethyl,N-morpholinoethyl aniline dihydrochlorine in 25 cc of water is added. The resulting reaction mixture is agitated for two hours at 30° C at which time it is filtered to recover the precipitate which has formed, said precipitate being the above product. The precipitate is then washed with water, recrystallized in a mixture of dimethylformamide and water, and dried under a vacuum. The resulting product exhibited a melting point of 195° C.

| Analysis | Calculated For C₂₂H₃₀N₄O₄ | Found | |
|---|---|---|---|
| C% | 63.75 | 63.45 | 63.58 |
| H% | 7.30 | 7.23 | 7.37 |
| N% | 13.52 | 13.32 | 13.55 |

EXAMPLE 30

Preparation of 2-N-β-hydroxyethylamino-5-[4'-N-(dibutylamino)anilino]-1,4-benzoquinone of the formula:

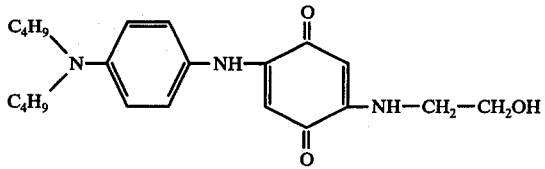

Into 20 cc of ethanol (96°) there are introduced (a) 0.01 mole (1.83 g) of 3-N-β-hydroxyethylamino-4-methoxy phenol and (b) 0.01 mole (2.70 g) of 4-nitroso dibutylaniline hydrochloride. The resulting reaction is left to stand, with agitation, for one hour at ambient temperature at which time it is filtered to recover the precipitate which has formed, which precipitate is the above product in the hydrochloride form thereof. This hydrochloride is dissolved in 30 cc of water and then alkalinized to a pH of 8 by the addition thereto of ammonia (22° Be) to precipitate the above 1,4-benzoquinone in the form of green crystals. After recrystallization in a mixture of dimethylformamide and water and drying under a vacuum, the product exhibited a melting point of 170° C.

| Analysis | Calculated For C₂₂H₃₁N₃O₃ | Found | |
|---|---|---|---|
| C% | 68.54 | 68.76 | 68.72 |
| H% | 8.11 | 8.14 | 7.98 |
| N% | 10.90 | 10.97 | 10.96 |

EXAMPLE 31

Preparation of 2-N-β-hydroxyethylamino-5-[2'-methyl-4'-(N-ethyl, N-β-benzoylaminoethyl)amino anilino]-1,4-benzoquinone of the formula:

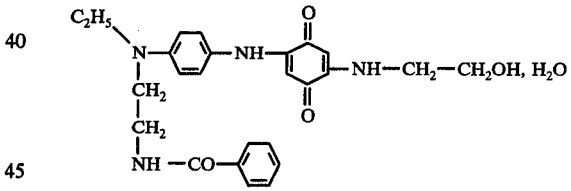

Into 20 cc of ethanol (96°) there are introduced (a) 0.01 mole (1.83 g) of 3-N-β-hydroxyethylamino-4-methoxy phenol, and (b) 0.01 mole (3.47 g) of 3-methyl-4-nitroso-N-ethyl,N-β-benzoylamino ethyl aniline hydrochloride. The resulting reaction mixture is left to stand, with agitation, for one hour at 50° C at which time it is filtered. The resulting filtrate is diluted by the addition thereto of 30 cc of water and alkalinized up to a pH of 8 by addition of ammonia (22° Be) and then filtered to recover the above substituted 1,4-benzoquinone which is then washed with water and recrystallized in a mixture of dimethylformamide and water. After drying under a vacuum the product exhibited a melting point of 104° C.

| Analysis | Calculated For C₂₆H₃₀O₄N₄ . H₂O | Found | |
|---|---|---|---|
| C% | 64.98 | 64.85 | 64.77 |
| H% | 6.71 | 6.94 | 6.83 |
| N% | 11.66 | 11.47 | 11.52 |

EXAMPLE 32

Preparation of 2-N-β-hydroxyethylamino-5-[4'-morpholino anilino]-1,4-benzoquinone of the formula:

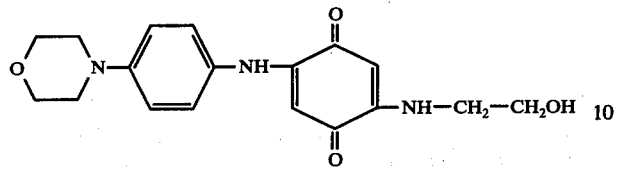

0.015 mole (2.74 g) of 3-β-hydroxyethylamino-4-methoxy phenol is dissolved in 15 cc of acetone to which have been added 10 cc of ammonia (22° Be). To this solution there are added 100 cc of $H_2O_2$ (20 volumes) and immediately thereafter, with agitation, 0.01 mole (1.78 g) of 4-N-[(amino)phenyl]morpholine in 25 cc of acetone. The resulting reaction mixture is agitated for 7 hours at ambient temperature at which time it is filtered to recover the precipitate which has formed, said precipitate being the above product. The precipitate is washed with water, recrystallized in dimethylformamide and dried under a vacuum. The product is chromatographically pure and melts above 260° C.

| Analysis | Calculated For $C_{18}H_{21}N_3O_4$ | Found | |
|---|---|---|---|
| C% | 62.96 | 62.40 | 62.78 |
| H% | 6.16 | 6.03 | 6.24 |
| N% | 12.24 | 12.00 | 12.17 |

EXAMPLES OF USE

EXAMPLE 33

The following solution is prepared:

| | |
|---|---|
| Dye of Example 5 | 0.2 g |
| Butyl glycol | 5.0 g |
| Lauryl alcohol oxyethylenated with 10.5 moles of ethylene oxide | 5.0 g |
| Ammonia (22° Be') q.s.p. | pH 9 |
| Water, q.s.p. | 100.0 g |

This solution is applied to bleached hair for a period of 20 minutes at 35° C. After rinsing and shampooing there is imparted thereto a very silvery almond green coloration.

EXAMPLE 34

The following solution is prepared:

| | |
|---|---|
| Dye of Example 5 | 0.025 g |
| Copolymer of 90% vinyl acetate-10% crotonic acid (MW = 45,000 – 50,000) | 2.0 g |
| Ethyl alcohol (96°) | 50.0 g |
| Water | 100.0 g |
| Triethanolamine, q.s.p. | pH 5 |

This hair setting lotion when applied to bleached hair imparts thereto a pearly appearance with green glints.

EXAMPLE 35

The following solution is prepared:

| | |
|---|---|
| Dye of Example 7 | 0.25 g |
| Ethyl alcohol (96°) | 40.0 g |
| Water, q.s.p. | 100.0 g |
| 10% solution of lactic acid, q.s.p. | pH 4.5 |

This solution when applied to bleached hair for 15 minutes at 30° C. after rinsing and shampooing imparts thereto a very dark green coloration with golden glints.

EXAMPLE 36

The following solution is prepared:

| | |
|---|---|
| Dye of Example 8 | 0.15 g |
| Ethyl alcohol (96°) | 25.0 g |
| Water, q.s.p. | 100.0 g |
| Ammonia (22° Be'), q.s.p. | pH 9 |

This solution when applied to 95% naturally white hair for 20 minutes at ambient temperature, after rinsing and shampooing, imparts thereto a silvery gray-green coloration.

EXAMPLE 37

The following solution is prepared:

| | |
|---|---|
| Dye of Example 5 | 0.025 g |
| Ethyl alcohol (96°) | 25.0 g |
| Water, q.s.p. | 100.0 g |
| Ammonia (22° Be') q.s.p. | pH 10 |

This solution when applied to bleached hair for 20 minutes at 35° C, after rinsing and shampooing imparts thereto a pearly pale green coloration.

EXAMPLE 38

The following solution is prepared:

| | |
|---|---|
| Dye of Example 8 | 0.15 g |
| Ethyl alcohol (96°) | 30.0 g |
| Water, q.s.p. | 100.0 g |
| Ammonia (22° Be') q.s.p. | pH 8 |

This solution when applied to bleached hair for 20 minutes at 40° C, after rinsing and shampooing imparts thereto a dark green coloration with golden glints.

EXAMPLE 39

The following solution is prepared:

| | |
|---|---|
| Dye of Example 10 | 0.1 g |
| Butylglycol | 5.0 g |
| Lauryl alcohol oxyethylenated with 10.5 moles of ethylene oxide | 5.0 g |
| Ammonia (22° Be') q.s.p. | pH 7.5 |
| Water, q.s.p. | 100.0 g |

This solution when applied to bleached hair for 20 minutes at ambient temperature, after rinsing and shampooing imparts thereto a silvery pale green coloration.

EXAMPLE 40

The following solution is prepared:

| | |
|---|---|
| Dye of Example 16 | 0.25 g |
| Butylglycol | 5.0 g |
| Lauryl alcohol oxyethylenated with 10.5 moles of ethylene oxide | 5.0 g |
| Ammonia (22° Be') q.s.p. | pH 9 |

This solution when applied to 95% naturally white hair for 20 minutes at 30° C, after rinsing and shampooing imparts thereto a very silvery dark green coloration.

EXAMPLE 41

The following solution is prepared:

| | |
|---|---|
| Dye of Example 7 | 0.2 g |
| Copolymer of 90% vinyl acetate-10% crotonic acid (MW = 45,000 – 50,000) | 2.0 g |
| Ethyl alcohol (96°) | 50.0 g |
| Water, q.s.p. | 100.0 g |
| Triethanolamine, q.s.p. | pH 7 |

This hair setting lotion when applied to bleached hair imparts thereto a pearly almond green coloration.

EXAMPLE 42

The following solution is prepared:

| | |
|---|---|
| Dye of Example 7 | 0.05 g |
| Ethyl alcohol (96°) | 40.0 g |
| Water, q.s.p. | 100.0 g |
| Ammonia (22° Be'), q.s.p. | pH 8 |

This solution when applied to bleached hair for 20 minutes at 30° C, after rinsing and shampooing imparted thereto a light green coloration with golden glints.

EXAMPLE 43

The following solution is prepared:

| | |
|---|---|
| Dye of Example 8 | 0.025 g |
| Water, q.s.p. | 100.0 g |
| Ammonia (22° Be'), q.s.p. | pH 9.5 |

This solution when applied to bleached hair for 20 minutes at ambient temperature, after rinsing and drying imparted thereto a pearly almond green coloration.

EXAMPLE 44

The following solution is prepared:

| | |
|---|---|
| Dye of Example 7 | 0.1 g |
| Ethyl alcohol (96°) | 30.0 g |
| Water, q.s.p. | 100.0 g |
| Ammonia (22° Be'), q.s.p. | pH 10.5 |

This solution when applied to 90% naturally white hair for 20 minutes at 40° C, after rinsing and shampooing imparted thereto a metallic green coloration.

EXAMPLE 45

The following solution is prepared:

| | |
|---|---|
| Dye of Example 11 | 0.15 g |
| Ethyl alcohol (96°) | 20.0 g |
| Water, q.s.p. | 100.0 g |
| Ammonia (22° Be'), q.s.p. | pH 7 |

This solution when applied to bleached hair for 20 minutes at 30° C, after rinsing and shampooing imparted thereto a pearly almond green coloration.

EXAMPLE 46

The following solution is prepared:

| | |
|---|---|
| Dye of Example 5 | 0.1 g |
| Copolymer of 90% vinyl acetate-10% crotonic acid (MW = 45,000 – 50,000) | 1.0 g |
| Ethyl alcohol (96°) | 36.0 g |
| Water, q.s.p. | 100.0 g |
| Triethanolamine, q.s.p. | pH 8 |

This hair setting lotion when applied to bleached hair imparts thereto a very luminous silvery pale green coloration.

EXAMPLE 47

The following solution is prepared:

| | |
|---|---|
| Dye of Example 9 | 0.1 g |
| Copolymer of 90% vinyl acetate-10% crotonic acid (MW = 45,000 – 50,000) | 1.0 g |
| Ethyl alcohol (96°) | 36.0 g |
| Water, q.s.p. | 100.0 g |
| Triethanolamine, q.s.p. | pH 7 |

This hair setting lotion when applied to bleached hair imparts thereto a light bronze coloration.

EXAMPLE 48

The following solution is prepared:

| | |
|---|---|
| Dye of Example 9 | 0.1 g |
| Ethyl alcohol (96°) | 20.0 g |
| Water, q.s.p. | 100.0 g |
| Ammonia (22° Be') q.s.p. | pH 9 |

This solution when applied to bleached hair for 20 minutes at 40° C, after rinsing and shampooing imparts thereto a linden coloration.

EXAMPLE 49

The following solution is prepared:

| | |
|---|---|
| Dye of Example 6 | 0.1 g |
| Copolymer of 90% vinyl acetate-10% crotonic acid (MW = 45,000 – 50,000) | 2.0 g |
| Ethyl alcohol (96°) | 50.0 g |
| Water, q.s.p. | 100.0 g |
| Ammonia (22° Be'), q.s.p. | pH 6 |

This hair setting lotion when applied to bleached hair imparts thereto a silvery almond green coloration.

EXAMPLE 50

The following solution is prepared:

| | |
|---|---|
| Dye of Example 14 | 0.15 g |
| Copolymer of 90% vinyl acetate-10% crotonic acid (MW = 45,000 – 50,000) | 1.0 g |
| Ethyl alcohol (96°) | 36.0 g |
| Water, q.s.p. | 100.0 g |
| Ammonia (22° Be'), q.s.p. | pH 8 |

This hair setting lotion when applied to bleached hair imparts thereto a pearly linden coloration.

EXAMPLE 51

The following solution is prepared:

| | |
|---|---|
| Dye of Example 17 | 0.15 g |
| Copolymer of 90% vinyl acetate-10% crotonic acid (MW = 45,000 – 50,000) | 2.0 g |
| Ethyl alcohol (96°) | 50.0 g |
| Water, q.s.p. | 100.0 g |
| Triethanolamine, q.s.p. | pH 6.5 |

This hair setting lotion when applied to bleached hair imparts thereto a very luminous palm tree green coloration.

EXAMPLE 52

The following solution is prepared:

| | |
|---|---|
| Dye of Example 3 | 0.1 g |
| Butyl glycol | 5.0 g |
| Lauryl alcohol oxyethylenated with 10.5 moles of ethylene oxide | 5.0 g |
| Ammonia (22° Be') q.s.p. | pH 8 |
| Water, q.s.p. | 100.0 g |

This solution when applied to bleached hair for 20 minutes at 40° C, after rinsing and drying imparted thereto a pearly light green coloration.

EXAMPLE 53

The following solution is prepared:

| | |
|---|---|
| Dye of Example 15 | 0.2 g |
| Ethyl alcohol (96°) | 40.0 g |
| Water, q.s.p. | 100.0 g |
| Ammonia (22° Be'), q.s.p. | pH 9.5 |

This solution when applied to bleached hair for 20 minutes at ambient temperature, after rinsing and shampooing imparted thereto a pearly appearance with silvery green glints.

EXAMPLE 54

The following solution is prepared:

| | |
|---|---|
| Dye of Example 7 | 0.05 g |
| Copolymer of 90% vinyl acetate-10% crotonic acid (MW = 45,000 – 50,000) | 2.0 g |
| Ethyl alcohol (96°) | 50.0 g |
| Water, q.s.p. | 100.0 g |
| Ammonia (22° Be'), q.s.p. | pH 9 |

This hair setting lotion when applied to bleached hair imparts thereto a light bronze green coloration with golden glints.

EXAMPLE 55

The following solution is prepared:

| | |
|---|---|
| Dye of Example 3 | 0.15 g |
| Copolymer of 90% vinyl acetate - 10% crotonic acid (MW=45,000 – 50,000) | 1.0 g |
| Ethyl alcohol (96°) | 360.0 g |
| Ammonia (22° Be'), q.s.p. | pH 5.5 |
| Water, q.s.p | 100.0 g |

This hair setting lotion when applied to bleached hair imparts thereto a vervain coloration.

EXAMPLE 56

The following solution is prepared:

| | |
|---|---|
| Dye of Example 1 | 0.1 g |
| Copolymer of 90% vinyl acetate - 10% crotonic acid (MW=45,000 – 50,000) | 2.0 g |
| Ethyl alcohol (96°) | 50.0 g |
| Water, q.s.p. | 100.0 g |
| Triethanolamine, q.s.p. | pH 7 |

This hair setting lotion when applied to bleached hair imparts thereto a beige coloration with metallic glints.

EXAMPLE 57

The following solution is prepared:

| | |
|---|---|
| Dye of Example 4 | 0.05 g |
| Copolymer of 90% vinyl acetate - 10% crotonic acid (MW=45,000 – 50,000) | 2.0 g |
| Ethyl alcohol (96°) | 50.0 g |
| Water, q.s.p. | 100.0 g |
| Triethanolamine, q.s.p. | pH 5 |

This hair setting lotion when applied to bleached hair imparts thereto a pearly light beige coloration with golden green glints.

EXAMPLE 58

The following solution is prepared:

| | |
|---|---|
| Dye of Example 2 | 0.1 g |
| Copolymer of 90% vinyl acetate - 10% crotonic acid (MW=45,000 – 50,000) | 2.0 g |
| Ethyl alcohol (96°) | 50.0 g |
| Ammonia (22° Be') q.s.p. | pH 6 |
| Water, q.s.p. | 100.0 g |

This hair setting lotion when applied to bleached hair imparts thereto a linden coloration.

EXAMPLE 59

The following solution is prepared:

| | |
|---|---|
| Dye of Example 13 | 0.1 g |
| Ethyl alcohol (96°) | 40.0 g |
| Water, q.s.p. | 100.0 g |
| Ammonia (22° Be'), q.s.p. | pH 10 |

This solution when applied to bleached hair for 20 minutes at 40° C. after rinsing and shampooing imparted thereto a pearly appearance with golden glints.

EXAMPLE 60

The following solution is prepared:

| | |
|---|---|
| Dye of Example 12 | 0.1 g |
| Copolymer of 90% vinyl acetate - 10% crotonic acid (MW=45,000 – 50,000) | 2.0 g |
| Ethyl alcohol (96°) | 50.0 g |
| Water, q.s.p. | 100.0 g |
| Ammonia (22° Be'),q.s.p. | pH 9 |

This hair setting lotion when applied to bleached hair imparts thereto a golden sand coloration.

EXAMPLE 61

The following solution is prepared:

| | | |
|---|---|---|
| Dye of Example 3 | 0.1 | g |
| Butylglycol | 5.00 | g |
| Lauryl alcohol oxyethylenated with 10.5 moles of ethylene oxide | 5.00 | g |
| N-[(4'-hydroxy)phenyl]-2,6-dimethyl benzoquinonimine | 0.20 | g |
| N-[(4'-dimethylamino)phenyl]-benzoquinoneimine | 0.05 | g |
| Water, q.s.p. | 100.0 | g |
| Ammonia (22° Be'), q.s.p. | pH 7.5 | |

This solution when applied to bleached hair for 10 minutes at 35° C, after rinsing and shampooing imparted thereto a steel blue gray coloration.

EXAMPLE 62

The following solution is prepared:

| | | |
|---|---|---|
| Dye of Example 7 | 0.075 | g |
| 4-methyl-2,5-diamino phenol dihydrochloride | 0.05 | g |
| Nitroparaphenylene diamine | 0.05 | g |
| Ethyl alcohol (96°) | 15.0 | g |
| Water, q.s.p. | 100.0 | g |
| Ammonia (22° Be'), q.s.p. | pH 9.5 | |

This solution when applied to 95% naturally white hair for 10 minutes at 35° C, after rinsing and shampooing imparted thereto a chestnut coloration with violet glints.

EXAMPLE 63

The following solution is prepared:

| | | |
|---|---|---|
| Dye of Example 9 | 0.1 | g |
| Nitroparaphenylene diamine | 0.05 | g |
| N-[(4'-amino)phenyl]-2-methyl-5-amino benzoquinoneimine | 0.05 | g |
| Copolymer of 90% vinyl acetate - 10% crotonic acid (MW=45,000 – 50,000) | 2.00 | g |
| Ethyl alcohol (96°) | 50.00 | g |
| Water, q.s.p. | 100.00 | g |
| Triethanolamine, q.s.p. | pH 6 | |

This hair setting lotion when applied to bleached hair imparts thereto a rose beige coloration with golden glints.

EXAMPLE 64

The following solution is prepared:

| | | |
|---|---|---|
| Dye of Example 16 | 0.15 | g |
| Nitroparaphenylene diamine | 0.1 | g |
| N-[(4'-amino)phenyl]-2-methyl-5-amino benzoquinoneimine | 0.15 | g |
| Butyl glycol | 5.00 | g |
| Lauryl alcohol oxyethylenated with 10.5 moles of ethylene oxide | 5.00 | g |
| Water, q.s.p. | 100.00 | g |
| Ammonia (22° Be') q.s.p. | pH 7.5 | |

This solution when applied to bleached hair for 20 minutes at ambient temperature, after rinsing and shampooing imparts thereto a golden bronze coloration.

EXAMPLE 65

The following solution is prepared:

| | | |
|---|---|---|
| Dye of Example 5 | 0.15 | g |
| Acetate of toluene blue | 0.025 | g |
| 1-γ-aminopropylamino anthraquinone | 0.1 | g |
| Copolymer of 90% vinyl acetate - 10% crotonic acid (MW=45,000 – 50,000) | 1.0 | g |
| Ethyl alcohol (96°) | 36.0 | g |
| Water, q.s.p. | 100.0 | g |
| Ammonia (22° Be'), q.s.p. | pH 7 | |

This hair setting lotion when applied to bleached hair imparts thereto a tin gray coloration.

EXAMPLE 66

The following solution is prepared:

| | | |
|---|---|---|
| Dye of Example 18 | 0.1 | g |
| Copolymer of 90% vinyl acetate - 10% crotonic acid (MW=45,000 – 50,000) | 2.0 | g |
| Ethyl alcohol (96°) | 50.0 | g |
| Water, q.s.p. | 100.0 | g |
| Ammonia (22° Be') q.s.p. | pH 8 | |

This hair setting lotion when applied to bleached hair imparts thereto a silvery beige coloration with green glints.

EXAMPLE 67

The following solution is prepared:

| | | |
|---|---|---|
| Dye of Example 19 | 0.1 | g |
| Copolymer of 90% vinyl acetate - 10% crotonic acid (MW=45,000 – 50,000) | 2.0 | g |
| Ethyl alcohol (96°) | 50.0 | g |
| Water, q.s.p. | 100.0 | g |
| Triethanolamine, q.s.p. | pH 7 | |

This hair setting lotion when applied to bleached hair imparts thereto a pearly almond green coloration.

EXAMPLE 68

The following solution is prepared:

| | | |
|---|---|---|
| Dye of Example 20 | 0.15 | g |
| Copolymer of vinyl acetate-crotonic acid (Example 67) | 2.0 | g |
| Ethyl alcohol (96°) | 50.0 | g |
| Water, q.s.p. | 100.0 | g |
| Triethanolamine, q.s.p. | pH 7 | |

This hair setting lotion when applied to bleached hair imparts thereto a golden light bronze coloration.

EXAMPLE 69

The following solution is prepared:

| | | |
|---|---|---|
| Dye of Example 21 | 0.125 | g |
| Ethyl alcohol (96°) | 40.0 | g |
| Water, q.s.p. | 100.0 | g |
| Lactic acid, q.s.p. | pH 5 | |

This solution when applied to bleached hair for 20 minutes at ambient temperature, after rinsing and shampooing, imparts thereto a metallic green coloration.

EXAMPLE 70

The following solution is prepared:

| Dye of Example 25 | 0.15 g |
| Copolymer of 90% vinyl acetate - 10% crotonic acid (MW=45,000 - 50,000) | 2.0 g |
| Ethyl alcohol (96°) | 50.0 g |
| Water, q.s.p. | 100.0 g |
| Triethanolamine, q.s.p. | pH 7 |

This hair setting lotion when applied to bleached hair imparts thereto a pearly light green coloration.

EXAMPLE 71

The following solution is prepared:

| Dye of Example 28 | 0.25 g |
| Copolymer of 90% vinyl acetate - 10% crotonic acid (MW=45,000 - 50,000) | 2.0 g |
| Ethyl alcohol (96°) | 50.0 g |
| Water, q.s.p. | 100.0 g |
| Triethanolamine, q.s.p. | pH 7 |

This hair setting lotion when applied to bleached hair imparts thereto a silvery almond green coloration.

EXAMPLE 72

The following solution is prepared:

| Dye of Example 27 | 0.1 g |
| Copolymer of 90% vinyl acetate - 10% crotonic acid (MW=45,000 - 50,000) | 2.0 g |
| Ethyl alcohol (96°) | 50.0 g |
| Water, q.s.p. | 100.0 g |
| Triethanolamine, q.s.p. | pH 8 |

This hair setting lotion when applied to bleached hair imparts thereto a vervain coloration.

EXAMPLE 73

The following solution is prepared:

| Dye of Example 24 | 0.1 g |
| Copolymer of 90% vinyl acetate - 10% crotonic acid (MW=45,000 - 50,000) | 2.0 g |
| Ethyl alcohol (96°) | 50.0 g |
| Water, q.s.p. | 100.0 g |
| Ammonia (22° Be'), q.s.p. | pH 9 |

This hair setting lotion when applied to bleached hair imparts thereto a linden green coloration.

EXAMPLE 74

The following solution is prepared:

| Dye of Example 22 | 0.05 g |
| Water, q.s.p. | 100.0 g |
| Ammonia (22° Be'), q.s.p. | pH 9.5 |

This solution when applied to 95% naturally white hair for 20 minutes at ambient temperature, after rinsing and shampooing imparts thereto a metallic dark green coloration.

EXAMPLE 75

The following solution is prepared:

| Dye of Example 23 | 0.25 g |
| Copolymer of 90% vinyl acetate - 10% crotonic acid (MW=45,000 - 50,000) | 2.0 g |
| Ethyl alcohol (96°) | 50.0 g |
| Water, q.s.p. | 100.0 g |
| Triethanolamine, q.s.p. | pH 6 |

This hair setting lotion when applied to bleached hair imparts thereto a light bronze green coloration.

EXAMPLE 76

The following solution is prepared:

| Dye of Example 26 | 0.15 g |
| Ethyl alcohol (96°) | 35.0 g |
| Water, q.s.p. | 100.0 g |
| Ammonia (22° Be'), q.s.p. | pH 10 |

This solution when applied to 95% naturally white hair for 20 minutes at 30° C imparts thereto, after rinsing and shampooing, a very silvery almond green coloration.

EXAMPLE 77

The following solution is prepared:

| Dye of Example 31 | 0.005 g |
| Isopropanol | 20.0 g |
| Butyl monoester of the copolymer of methyl vinyl ether/maleic anhydride (sold by GAF under the trade name ES 421) | 1.0 g |
| 2-amino-2-methyl propanol, q.s.p. | pH 7 |
| Water, q.s.p. | 100.0 g |

This hair setting lotion when applied to previously bleached hair, after drying imparts thereto an ash blond coloration with greenish glints.

EXAMPLE 78

The following solution is prepared:

| Dye of Example 29 | 0.5 g |
| Copolymer of 70% polyvinyl pyrrolidone 30% vinylacetate (MW=40,000) | 3.0 g |
| Ethyl alcohol (96°) | 70.0 g |
| 2-amino-2-methyl propanol, q.s.p. | pH 8 |
| Water, q.s.p. | 100.0 g |

This hair setting lotion when applied to white hair imparted thereto, after drying, a bronze green coloration.

EXAMPLE 79

The following solution is prepared:

| Dye of Example 30 | 0.25 g |
| Isopropanol | 50.0 g |
| Copolymer of 40% polyvinyl pyrrolidone - 60% vinyl acetate (MW=100.000) | 2.0 g |
| Monoethanolamine, q.s.p. | pH 9.5 |
| Water, q.s.p. | 100.0 g |

This hair setting lotion when applied to gray hair imparts thereto after drying a seal gray coloration.

EXAMPLE 80

The following solution is prepared:

| | |
|---|---|
| Dye of Example 2 | 0.2 g |
| Ethyl alcohol (96°) | 60.0 g |
| Copolymer of 30% polyvinyl pyrrolidone 70% vinyl acetate (MW=160,000) | 1.0 g |
| Ammonia (22° Be'), q.s.p. | pH 7.5 |
| Water, q.s.p. | 100.0 g |

This hair setting lotion when applied to bleached hair imparts thereto after drying a camomile coloration.

EXAMPLE 81

The following solution is prepared:

| | |
|---|---|
| Dye of Example 6 | 0.1 g |
| Isopropanol | 30.0 g |
| Polyvinylpyrrolidone (MW=40,000) | 3.0 g |
| Triethanolamine, q.s.p. | pH 10 |
| Water, q.s.p. | 100.0 g |

This hair setting lotion when applied to white hair imparts thereto after drying a linden coloration.

EXAMPLE 82

The following solution is prepared:

| | |
|---|---|
| Dye of Example 11 | 0.1 g |
| Ethanol (96°) | 50.0 g |
| Terpolymer of 80% vinyl acetate, 15% allyl stearate, 5% allyloxy-acetic acid viscosity (5% DMF solution-ebullition of ether)4.4–5 cps | 1.5 g |
| Monoethanolamine, q.s.p. | pH 6 |
| Water q.s.p. | 100.0 g |

This hair setting lotion when applied to gray hair imparts thereto after drying a greenish yellow coloration.

EXAMPLE 83

The following solution is prepared:

| | |
|---|---|
| Dye of Example 29 | 0.2 g |
| Polyethylene glycol tertiary dodecyl thio ether | 5.0 g |
| Stearyl alcohol | 20.0 g |
| Sodium cetyl stearyl sulfate | 3.0 g |
| Ethyl alcohol (96°) | 10.0 g |
| Diethanolamide of coconut and coprah | 4.0 g |
| Acetic acid, q.s.p. | pH 8 |
| Water, q.s.p. | 100.0 g |

This cream is applied for 15 minutes to previously bleached hair. After rinsing, shampooing, rinsing and drying there is imparted thereto a greenish blond coloration with golden glints.

EXAMPLE 84

The following solution is prepared:

| | |
|---|---|
| Dye of Example 2 | 0.05 g |
| N-[(6-hydroxy-1-oxa-4-aza-1,2,3,4-tetrahydro-7-naphthyl]-3-methoxy benzoquinone diimine | 0.05 g |
| Amino acetate of N-[(4'-amino-2'-methoxy-5'-methyl)vinyl]-3-amino-2-aza benzoquinone diimine | 0.05 g |
| 4,4'-dihydroxy-2-amino azo benzene | 0.05 g |
| Butyl glycol | 5.0 g |
| Monoethanolamine, q.s.p. | pH 9.5 |
| Water, q.s.p. | 100.0 g |

This solution when applied to white hair for 25 minutes imparts thereto, after rinsing, shampooing, rinsing and drying a bottle green coloration.

The same solution when applied to gray hair imparts thereto a pine green coloration.

What is claimed is:

1. Diaminobenzoquinone of the formula

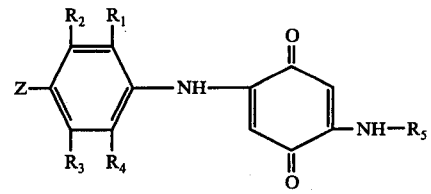

wherein $R_1$, $R_2$, $R_3$ and $R_4$ each independently represent a member selected from the group consisting of hydrogen, halogen, lower alkyl and lower alkoxy;

$R_5$ represents a member selected from the group consisting of hydrogen, lower alkyl, hydroxy lower alkyl and amino alkyl of the formula

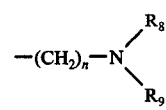

wherein $n$ is 2–6 and $R_8$ and $R_9$ each independently represent a member selected from the group consisting of hydrogen, lower alkyl and hydroxy lower alkyl; and Z is

wherein one of $R_6$ and $R_7$ is selected from the group consisting of hydrogen, lower alkyl, hydroxy lower alkyl, carbamyl lower alkyl, acetylamino lower alkyl, mesylamino lower alkyl, benzoylamino lower alkyl and

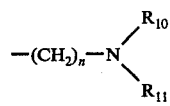

wherein $n$ is 2–6 and $R_{10}$ and $R_{11}$ each independently are selected from the group consisting of lower alkyl, hydroxy lower alkyl and acetylamino, and the other is

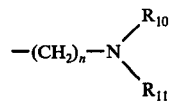

wherein $n$ is 2–6 and $R_{10}$ and $R_{11}$ together with the nitrogen atom to which they are attached form a heterocycle selected from the group consisting of piperidinyl and morpholinyl.

2. Diaminobenzoquinone of the formula

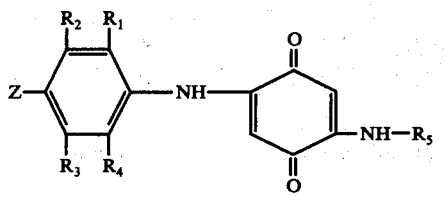

wherein $R_1$, $R_2$, $R_3$ and $R_4$ each independently represent a member selected from the group consisting of hydrogen, halogen, lower alkyl and lower alkoxy;

$R_5$ represents a member selected from the group consisting of hydrogen, lower alkyl, hydroxy lower alkyl and amino alkyl of the formula

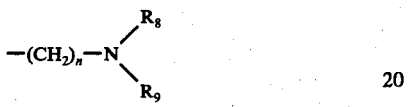

wherein $n$ is 2–6 and $R_8$ and $R_9$ each independently represent a member selected from the group consisting of hydrogen, lower alkyl and hydroxy lower alkyl; and Z is

wherein one of $R_6$ and $R_7$ is lower alkyl and the other is

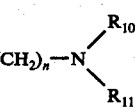

wherein $n$ is 2–6 and $R_{10}$ and $R_{11}$ together with the nitrogen atom to which they are attached form a heterocycle selected from the group consisting of piperidinyl and morpholinyl.

* * * * *